United States Patent [19]

Okazaki et al.

[11] Patent Number: 4,895,931

[45] Date of Patent: Jan. 23, 1990

[54] PHOSPHOLIPASE A$_2$-INHIBITING PEPTIDES

[75] Inventors: Kei Okazaki; Akiko Saito; Moriyuki Sato, all of Machida, Japan

[73] Assignee: Kyowa Hakko Kogyo Co., Ltd., Tokyo, Japan

[21] Appl. No.: 301,477

[22] Filed: Jan. 26, 1989

[30] Foreign Application Priority Data

Feb. 4, 1988 [JP] Japan .................................. 63-24572

[51] Int. Cl.$^4$ .............................................. C07K 7/08
[52] U.S. Cl. .................................... 530/326; 530/324; 530/325
[58] Field of Search ......................... 530/324, 325, 326

[56] References Cited

U.S. PATENT DOCUMENTS

| | | | |
|---|---|---|---|
| 4,624,852 | 11/1986 | Wurtman | 514/76 |
| 4,737,489 | 4/1988 | Wurtman | 514/76 |
| 4,775,665 | 10/1988 | Wurtman | 514/419 |
| 4,778,304 | 11/1988 | Marshall et al. | 514/886 |

OTHER PUBLICATIONS

Wallner, et al., "Cloning and Expression of Human Lipocortin, A Phospholipase A$_2$ Inhibitor with Potential Anti—Inflammatory Activity", Nature, 320, 77, (1986).

Huang, et al., "Purification and Characterization of Proteolytic Fragments of Lipocortin I That Inhibit Phospholipase A$_2$", J. Biol. Chem., 262, 7639, (1987).

*Primary Examiner*—Lester L. Lee
*Attorney, Agent, or Firm*—Fitzpatrick, Cella, Harper & Scinto

[57] ABSTRACT

Disclosed are peptides which have amino acid sequences consisting of 15 to 26 amino acid constituents and have phospholipase A$_2$-inhibiting activity.

1 Claim, No Drawings

PHOSPHOLIPASE A₂-INHIBITING PEPTIDES

BACKGROUND OF THE INVENTION

The present invention relates to novel peptides inhibiting phospholipase A₂ (hereinafter referred to as PLA₂) activity.

It has been known that lipocortin is a protein having an amino acid sequence consisting of 346 constituents, a molecular weight of about 37,000 and anti-inflammatory activity, and exhibits an inhibitory activity against PLA₂, an enzyme which induces the formation of inflammation-causing substances [Nature, 320, 77 (1986)]. However, lipocortin is a large molecule protein and is not always suitable for the use in anti-inflammatory drugs in view of the problems such as lack of stability and restriction on administration method.

Further, it has been disclosed that as the amino terminal groups or the carboxyl terminal groups of lipocortin are eliminated, its remaining PLA₂-inhibiting activity gradually decreases, and a protein having a molecular weight of about 15,000 and which exhibits an inhibitory activity of about 4% of that of lipocortin has been disclosed as the smallest lipocortin fragment having the activity [J. Biol. Chem., 262, 7639 (1987)].

SUMMARY OF THE INVENTION

The present invention provides novel peptides having an excellent PLA₂-inhibiting activity.

DETAILED DESCRIPTION OF THE INVENTION

The present invention relates to peptides which have amino acid sequences consisting of 15 to 26 constituents and have phospholipase A₂-inhibiting activity. More specifically, the present invention relates to the peptides having the amino acid sequences represented by the following formulae (I) to (XII), respectively:

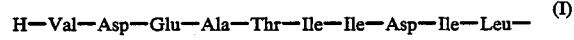

(I)

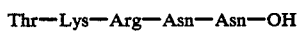

(II)

(III)

(IV)

(V)

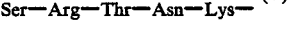

(VI)

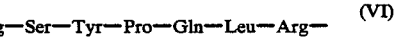

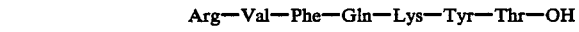

(VII)

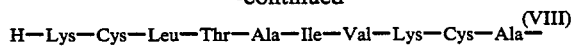

(VIII)

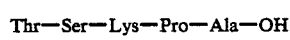

(IX)

(X)

(XI)

(XII)

The above Compounds (I) to (XII) are synthesized according to a solid phase synthetic method using an automated peptide synthesizer.

A solid phase carrier resin to which a peptide is bound as obtained by the solid phase method is treated with hydrogen fluoride, whereby the peptide is freed from the carrier resin and at the same time the protective groups on the amino acid side chains are removed. After rough purification by gel filtration column chromatography, the obtained crude peptide is purified by high performance liquid chromatography (hereinafter referred to as HPLC) using a reversed phase column to obtain a pure product Compounds (I) to (XII) are stable peptides which have amino acid sequences consisting of 15 to 26 constituents and a molecular weight of about 1500 to 2300 and exhibit excellent inhibiting activity against PLA₂.

The PLA₂-inhibiting activity of the compounds of the present invention is demonstrated by the following test example.

TEST EXAMPLE

PLA₂-inhibiting activity:

A test compound was dissolved in 280 μl of 0.1M Tris-hydrochloride buffer (pH 8.8) containing 10 mM calcium chloride. To the solution was added a solution of 20 ng of porcine pancreas PLA₂ (Sigma Chemical Co., catalog No. P6534) in 10 μl of the buffer having the same composition as above, followed by incubation at 37° C. for 10 minutes. To the resulting mixture was added a solution of 0.1 μCi of α-palmitoyl-β[1-$^{14}$C] arachidonylphosphatidylcholine (54 μCi/μmol, NEN Research Products Co.) in 10 μl of the same buffer as above wherein micelles were formed, followed by incubation at 37° C. for 10 minutes. Then, 3 ml of a Dale reagent solution [2-propanol :n-heptane :1M sulfuric acid=40:10:1 v/v mixture; Methods in Enzymology 14, 167 (1969)] was added to stop the reaction, and 1.5 ml of n-heptane and 1 ml of water were added, followed by shaking. Radioactivity of the free [1-$^{14}$C] arachidonic acid extracted to the heptane layer was measured. The value of this specific radioactivity is referred to as "a". Further, "b" and "c" refer to the specific radioactivity of the heptane layer obtained by adding the same amount of the buffer in place of the test compound solution and that of the heptane layer obtained by adding the same amount of the buffer in place of the test compound and PLA$_2$, respectively. The inhibition rate (x) was calculated by the following equation:

$$x(\%) = \frac{a - c}{b - c} \times 100$$

The results are shown in Table 1 as relative activity ratio based on the activity of Compound (IV) which exhibited a medium PLA$_2$-inhibiting activity.

TABLE 1

| Test Compound* | Inhibition ratio** | Test compound* | Inhibition ratio** |
|---|---|---|---|
| I | 0.50 | VII | 0.59 |
| II | 0.57 | VIII | 1.06 |
| III | 0.20 | IX | 0.41 |
| IV | 1.00 | X | 1.19 |
| V | 0.56 | XI | 0.49 |
| VI | 0.58 | XII | 1.57 |

*Amount of sample: 100 mg
**Inhibition rate of test compound/Inhibition rate of Compound (IV)

Further, Table 2 shows the results of determination of a concentration required for inhibiting the PLA$_2$ activity by 50% (IC$_{50}$).

rLC in the table means lipocortin prepared using *Escherichia coli* according to the method of Wallner, et al. (Nature, 320, 77 (1986)].

TABLE 2

| Test compound | IC$_{50}$ (μg/ml) |
|---|---|
| VIII | 50 |
| X | 30 |
| XII | 2 |
| rLC (Control compound) | 1.5 |

As is seen from Table 2, the compounds of the present invention exhibit a strong PLA$_2$-inhibiting activity. Particularly, Compound (XII) having an amino acid sequence consisting of 16 constituents and a molecular weight of 1864 exhibited IC$_{50}$ almost equal to that of lipocortin, although its molecular weight is about one twentieth of that of lipocortin.

Certain embodiments of the present invention are illustrated in the following examples. The following abbreviations are used for amino acids and their protective groups according to the recommendation [Biochemistry, 11, 1926 (1972)] of IUPAC-IUB Commission on Biochemical Nomenclature.

| | | | |
|---|---|---|---|
| Gly: | glycine | Ala: | L—alanine |
| Val: | L—valine | Leu: | L—leucine |
| Ile: | L—isoleucine | Ser: | L—serine |
| Thr: | L—threonine | Asp: | L—aspartic acid |
| Asn: | L—asparagine | Glu: | L—glutamic acid |
| Gln: | L—glutamine | Lys: | L—lysine |
| Met: | L—methionine | His: | L—histidine |
| Arg: | L—arginine | Phe: | L—phenylalanine |
| Tyr: | L—tyrosine | Cys: | L—cysteine |
| Pro: | L—proline | Asx: | aspartic acid or asparagine |
| Glx: | glutamic acid or glutamine | t-Boc: | t-butyloxycarbonyl |
| Bzl: | benzyl | CH$_3$—Bzl: | 4-methylbenzyl |
| Br—Z: | 2-bromobenzyloxycarbonyl | Cl—Z: | 2-chlorobenzyloxycarbonyl |
| Tos: | tosyl | | |

In the following examples, each peptide was synthesized using a 430A peptide synthesizer of Applied Biosystems, Inc., Foster City, Calif., U.S.A. (hereinafter referred to as ABI Inc.) and reagents and solvents of ABI Inc. according to the synthesis program of ABI Inc.

Further, condensing reactions were carried out under standard conditions according to the synthesis program of ABI Inc., wherein asparagine, glutamine and arginine were coupled in the form of an active ester with 1-hydroxybenzotriazole and the other amino acids were coupled in the form of a symmetrical acid anhydride.

EXAMPLE 1 Synthesis of Compound (IV)

A carrier resin (0.81 g) to which 0.5 mmol of t-Boc-Glu (OBzl) was bound was placed in the reaction vessel of the synthesizer. The following treatments and washing were carried out according to the synthesis program of ABI Inc.:

(1) Treatment with a methylene chloride solution containing 33% trifluoroacetic acid (80 seconds)

(2) Treatment with a methylene chloride solution containing 50% trifluoroacetic acid (18.5 minutes)

(3) Washing with methylene chloride (three times)

(4) Treatment with a methylene chloride solution containing 10% diisopropylethylamine (one minute, twice)

(5) Washing with dimethylformamide (five times)

(6) To the thus obtained carrier resin to which Glu (OBzl) was bound was added 4 ml of a dimethylformamide solution containing 1.0 mmol of the symmetrical acid anhydride of t-Boc-Leu, followed by stirring for 18 minutes in the reaction vessel.

(7) Washing with methylene chloride (five times)

Thus, t-Boc-Leu-Glu (OBzl) was synthesized on the carrier resin. Then, after the deprotecting steps of the above (1) to (5) were repeated, the symmetrical acid anhydride of t-Boc-His (Tos) was added to carry out a condensing reaction as in step (6) and then via the washing step of (7) t-Boc-His(Tos)-Leu-Glu (OBzl) was synthesized on the carrier resin. Further repetitions of steps (1) to (7) gave 1.90 g of the carrier resin to which a protected peptide was bound.

In step (6) in the above repeated procedures, t-Boc-Gly, t-Boc-Thr(Bzl), t-Boc-Leu, t-Boc-Ala, t-Boc-Lys(Cl-Z), t-Boc-Lys(Cl-Z), t-Boc-Leu, t-Boc-Thr(Bzl), t-Boc-Glu(OBzl), t-Boc-Asp(OBzl), t-Boc-Leu, t-Boc-Pro and t-Boc-Lys(Cl-Z) were used in turn.

After the completion of the synthesizing reaction, 0.5 ml of anisole was added to 0.4 g of the obtained carrier resin. The mixture was allowed to stand for 3 hours, and 5 ml of hydrogen fluoride was added, followed by stirring under ice cooling for one hour. Hydrogen fluoride was removed under reduced pressure, and 30 ml of ethyl acetate and 25 ml of 2 M acetic acid were added to the carrier resin, followed by stirring for one hour. The water layer separated was washed with 30 ml of ethyl acetate, applied to a column (2 cm×80 cm) of Sephadex G-25 (Pharmacia Fine Chemicals Inc.), and eluted with an aqueous 1 M acetic acid solution. Eluted fractions were analyzed by measuring the absorbance at 274 nm to obtain fractions containing Compound (IV). The fractions were combined and freeze-dried to obtain 136 mg of the crude peptide. Then, 25 mg of this preparation was dissolved in 2.3 ml of aqueous 0.1% trifluoroacetic acid solution and purified by HPLC using a reversed column (NUCLEOSIL 5C18; φ20×250 mm). Elution was carried out by the linear concentration gradient method using 0.1% trifluoroacetic acid and an acetonitrile solution of 0.1% trifluoroacetic acid. The effluent was monitored at 220 nm, and the pooled fractions containing Compound (IV) were obtained. These fractions were combined and freeze-dried to obtain 10.7 mg of Compound (IV) in a pure state.

Mass spectrum (SIMS; the same shall apply hereinafter): 1853 (M+ +1)
Amino acid analysis:
Asx 0.7(1), Glx 1.9(2), Gly 1.1(1), His 1.1(1),
Thr 2.0(2), Ala 1.0(1), Pro 1.0(1), Leu 3.9(4),
Lys 3.2(3)

EXAMPLE 2 Synthesis of Compound (I)

A carrier resin to which a protected peptide was bound (1.36 g) was obtained in the same manner as in Example 1 using a carrier resin to which t-Boc-Asn was bound and the following protected amino acids:
t-Boc-Asn, t-Boc-Arg(Tos), t-Boc-Lys(Cl-Z), t-Boc-Thr(Bzl), t-Boc-Leu, t-Boc-Ile, t-Boc-Asp(OBzl), t-Boc-Ile, t-Boc-Ile, t-Boc-Thr(Bzl), t-Boc-Ala, t-Boc-Glu(OBzl), t-Boc-Asp(OBzl) and t-Boc-Val.

The obtained carrier resin (0.40 g) was subjected to the same hydrogen fluoride treatment and gel filtration column chromatography as in Example 1 to obtain 100 mg of the crude peptide. Then, 25 mg of this preparation was purified by HPLC to obtain 8.6 mg of Compound (I) in a pure state.

Mass spectrum: 1714 (M+ +1)
Amino acid analysis:
Asx 4.1(4), Glx 1.4(1), Arg 0.7(1), Thr 1.5(2),
Ala 1.5(1), Leu 0.9(1), Ile 2.2(3), Val 0.9(1),
Lys 1.1(1)

EXAMPLE 3 Synthesis of Compound (II)

A carrier resin to which a protected peptide was bound (1.29 g) was obtained in the same manner as in Example 1 using a carrier resin to which t-Boc-Tyr(Br-Z) was bound and the following protected amino acids:
t-Boc-Ala, t-Boc-Ala, t-Boc-Lys(Cl-Z), t-Boc-Ile, t-Boc-Gln, t-Boc-Gln, t-Boc-Arg(Tos), t-Boc-Gln, t-Boc-Ala, t-Boc-Asn, t-Boc-Asn, t-Boc-Arg(Tos), t-Boc-Lys(Cl-Z) and t-Boc-Thr(Bzl).

The obtained carrier resin (0.40 g) was subjected to the same hydrogen fluoride treatment and gel filtration column chromatography as in Example 1 to obtain 136 mg of the crude peptide. Then, 25 mg of this preparation was purified by HPLC to obtain 4.2 mg of Compound (II) in a pure state.

Mass spectrum: 1789 (M+ +1)
Amino acid analysis:
Asx 2.1(2), Glx 3.2(3), Arg 1.8(2), Thr 0.9(1),
Ala 2.8(3), Tyr 1.2(1), Ile 1.1(1), Lys 2.0(2)

EXAMPLE 4 Synthesis of Compound (III)

To 0.40 g of the carrier resin to which the protected peptide was bound as obtained in Example 1, were bound t-Boc-Gly, t-Boc-Thr(Bzl), t-Boc-Glu(OBzl), t-Boc-Gln and t-Boc-Leu in turn as protected amino acids in the same manner as in Example 1 to obtain 0.50 g of a carrier resin. To 0.25 g of the carrier resin were further bound t-Boc-Tyr(Br-Z), t-Boc-Ala, t-Boc-Ala, t-Boc-Lys(Cl-Z) and t-Boc-Ile in turn as protected amino acids in the same manner as in Example 1 to obtain 0.33 g of a carrier resin to which a protected peptide was bound.

The obtained carrier resin was subjected to the same hydrogen fluoride treatment and gel filtration column chromatography as in Example 1 to obtain 95 mg of the crude peptide. Then, 25 mg of this preparation was purified by HPLC to obtain 29.6 mg of Compound (III) in a pure state.

Mass spectrum : 2320 (M+ +1)
Amino acid analysis:
Asx 1.1(1), Glx 4.1(4), Gly 2.3(2), His 0.9(1),
Thr 2.7(3), Ala 1.1(1), Pro 1.1(1), Leu 4.7(5),
Lys 3.0(3)

EXAMPLE 5 Synthesis of Compound (V)

A carrier resin to which a protected peptide was bound (1.49 g) was obtained in the same manner as in Example 1 using a carrier resin to which t-Boc-Ile was bound and the following protected amino acids:
t-Boc-Asp(OBzl), t-Boc-Arg(Tos), t-Boc-Ile, t-Boc-Glu(OBzl), t-Boc-Lys(Cl-Z), t-Boc-Asn, t-Boc-Thr(Bzl), t-Boc-Arg(Tos), t-Boc-Ser(Bzl), t-Boc-Ala, t-Boc-Leu, t-Boc-Ile, t-Boc-Glu(OBzl) and t-Boc-Ile.

The obtained carrier resin (0.40 g) was subjected to the same hydrogen fluoride treatment and gel filtration column chromatography as in Example 1 to obtain 137 mg of the crude peptide. Then, 39 mg of this preparation was purified by HPLC to obtain 4.0 mg of Compound (V) in a pure state.

Mass spectrum: 1769 (M+ +1)
Amino acid analysis:
Asx 2.1(2), Glx 1.7(2), Ser 1.1(1), Arg 1.7(2),
Thr 1.0(1), Ala 1.0(1), Ile 4.4(4), Leu 0.9(1),
Lys 1.0(1)

EXAMPLE 6 Synthesis of Compound (VI)

A carrier resin to which a protected peptide was bound (1.85 g) was obtained in the same manner as in Example 1 using a carrier resin to which t-Boc-Thr(Bzl) was bound and the following protected amino acids:
t-Boc-Tyr(Br-Z), t-Boc-Lys(Cl-Z), t-Boc-Gln, t-Boc-Phe, t-Boc-Val, t-Boc-Arg(Tos), t-Boc-Arg(Tos), t-Boc-Leu, t-Boc-Gln, t-Boc-Pro, t-Boc-Tyr(Br-Z), t-Boc-Ser(Bzl), t-Boc-Arg(Tos), t-Boc-Thr(Bzl) and t-Boc-Thr(Bzl).

The obtained carrier resin (0.40 g) was subjected to the same hydrogen fluoride treatment and gel filtration column chromatography as in Example 1 to obtain 113 mg of the crude peptide. Then, 25 mg of this preparation was purified by HPLC to obtain 7.5 mg of Compound (VI) in a pure state.

Mass spectrum: 2043 (M+ +1)
Amino acid analysis:
Glx 2.0(2), Ser 1.0(1), Arg 3.0(3), Thr 3.1(3),
Pro 1.0(1), Tyr 2.0(2), Leu 1.1(1), Val 1.1(1),
Phe 1.0(1), Lys 1.1(1)

EXAMPLE 7 Synthesis of Compound (VII)

A carrier resin to which a protected peptide was bound (1.44 g) was obtained in the same manner as in Example using a carrier resin to which t-Boc-Ala was bound and the following protected amino acids:
t-Boc-Cys(CH3-Bzl), t-Boc-Lys(Cl-Z), t-Boc-Val, t-Boc-Ile, t-Boc-Ala, t-Boc-Thr(Bzl), t-Boc-Leu, t-Boc-Cys(CH3-Bzl), t-Boc-Lys(Cl-Z), t-Boc-Glu(OBzl), t-Boc-Ile, t-Boc-Asp(OBzl), t-Boc-Gly and t-Boc-Lys(Cl-Z).

The obtained carrier resin (0.40 g) was subjected to the same hydrogen fluoride treatment and gel filtration column chromatography as in Example 1 to obtain 117 mg of the crude peptide. Then, 25 mg of this preparation was purified by HPLC to obtain 7.4 mg of Compound (VII) in a pure state.

Mass spectrum: 1591 (M+ +1)

Amino acid analysis:
Asx 1.2(1), Glx 1.0(1), Gly 1.1(1), Thr 1.0(1),
Ala 2.1(2), Val 0.6(1), Cys 2.2(2), Ile 1.6(2),
Leu 1.0(1), Lys 3.4(3)

EXAMPLE 8 Synthesis of Compound (VIII)

A carrier resin to which a protected peptide was bound (1.48 g) was obtained in the same manner as in Example 1 using a carrier resin to which t-Boc-Ala was bound and the following protected amino acids:

t-Boc-Pro, t-Boc-Lys(Cl-Z), t-Boc-Ser(Bzl), t-Boc-Thr(Bzl), t-Boc-Ala, t-Boc-Cys(CH3-Bzl), t-Boc-Lys(Cl-Z), t-Boc-Val, t-Boc-Ile, t-Boc-Ala, t-Boc-Thr(Bzl), t-Boc-Leu, t-Boc-Cys(CH3-Bzl) and t-Boc-Lys(Cl-Z)

The obtained carrier resin (0.37 g) was subjected to the same hydrogen fluoride treatment and gel filtration column chromatography as in Example 1 to obtain 149 mg of the crude peptide. Then, 26 mg of this preparation was purified by HPLC to obtain 2.5 mg of Compound (VIII) in a pure state.

Mass spectrum 1774 ($M^+ + 1$)
Amino acid analysis:
Glx 1.0(1), Ser 1.2(1), Thr 2.0(2), Ala 3.1(3),
Pro 1.1(1), Val 0.6(1), Cys 2.2(2), Ile 1.5(2),
Leu 1.1(1), Lys 3.0(3)

EXAMPLE 9 Synthesis of Compound (IX)

A carrier resin to which a protected peptide was bound (1.71 g) was obtained in the same manner as in Example 1 using a carrier resin to which t-Boc-Lys(Cl-Z) was bound and the following protected amino acids:

t-Boc-Glu(OBzl), t-Boc-Ala, t-Boc-Phe, t-Boc-Phe, t-Boc-Ala, t-Boc-Pro, t-Boc-Lys(Cl-Z), t-Boc-Ser(Bzl), t-Boc-Thr(Bzl), t-Boc-Ala, t-Boc-Cys(CH3-Bzl), t-Boc-Lys(Cl-Z), t-Boc-Val and t-Boc-Ile The obtained carrier resin (0.39 g) was subjected to the same hydrogen fluoride treatment and gel filtration column chromatography as in Example 1 to obtain 77 mg of the crude peptide. Then, 25 mg of this preparation was purified by HPLC to obtain 6.7 mg of Compound (IX) in a pure state.

Mass spectrum: 1639 ($M^+ + 1$)
Amino acid analysis:
Glx 1.2(1), Ser 1.3(1), Thr 1.1(1), Ala 3.1(3),
Pro 1.4(1), Val 0.5(1), Cys 0.8(1), Ile 0.5(1),
Phe 2.1(2), Lys 2.9(3)

EXAMPLE 10 Synthesis of Compound (X)

A carrier resin to which a protected peptide was bound (1.37 g) was obtained in the same manner as in Example 1 using a carrier resin to which t-Boc-Arg(Tos) was bound and the following protected amino acids:

t-Boc-Ser(Bzl), t-Boc-Val, t-Boc-Met, t-Boc-Ile, t-Boc-Arg(Tos), t-Boc-Ile, t-Boc-Ala, t-Boc-Lys(Cl-Z), t-Boc-His(Tos), t-Boc-Arg(Tos), t-Boc-Thr(Bzl), t-Boc-Gly, t-Boc-Val and t-Boc-Gly The obtained carrier resin (0.40 g) was subjected to the same hydrogen fluoride treatment and gel filtration column chromatography as in Example 1 to obtain 144 mg of the crude peptide. Then, 25 mg of this preparation was purified by HPLC to obtain 4.0 mg of Compound (X) in a pure state.

Mass spectrum : 1853 ($M^+ + 1$)
Amino acid analysis:
Glx 0.8(1), Ser 1.9(2), Gly 1.1(1), His 0.9(1),
Arg 2.6(3), Thr 0.8(1), Ala 1.0(1), Val 1.3(1),
Met 1.3(1), Ile 2.1(2), Leu 1.0(1), Lys 1.1(1)

EXAMPLE 11 Synthesis of Compound (XI)

A carrier resin to which a protected peptide was bound (1.79 g) was obtained in the same manner as in Example 1 using a carrier resin to which t-Boc-Tyr(Br-Z) was bound and the following protected amino acids:

t-Boc-Phe, t-Boc-Ala, t-Boc-Lys(Cl-Z), t-Boc-Ile, t-Boc-Asp(OBzl), t-Boc-Asn, t-Boc-Met, t-Boc-Asp (OBzl), t-Boc-Ile, t-Boc-Glu(OBzl), t-Boc-Ser(Bzl), t-Boc-Arg(Tos), t-Boc-Ser(Bzl) and t-Boc-Val.

The obtained carrier resin (0.40 g) was subjected to the same hydrogen fluoride treatment and gel filtration column chromatography as in Example 1 to obtain 54 mg of the crude peptide. Then, 25 mg of this preparation was purified by HPLC to obtain 10.2 mg of Compound (XI) in a pure state.

Mass spectrum: 1787 ($M^+ + 1$)
Amino acid analysis:
Asx 3.0(3), Gly 1.1(1), Ser 2.0(2), Arg 1.1(1),
Ala 1.0(1), Thr 1.1(1), Val 1.0(1), Met 0.9(1),
Ile 1.9(2), Phe 1.0(1), Lys 0.9(1)

EXAMPLE 12 Synthesis of Compound (XII)

A carrier resin to which a protected peptide was bound (1.39 g) was obtained in the same manner as in Example 1 using a carrier resin to which t-Boc-Ala was bound and the following protected amino acids:

t-Boc-Gln, t-Boc-Cys(CH3-Bzl), t-Boc-Leu, t-Boc-Ser(Bzl), t-Boc-Ile, t-Boc-Gly, t-Boc-Tyr(Br-Z), t-Boc-Met, t-Boc-Lys(Cl-Z), t-Boc-Gln, t-Boc-Tyr(Br-Z), t-Boc-Phe, t-Boc-Ala, t-Boc-Lys(Cl-Z) and t-Boc-Ile The obtained carrier resin (0.39 g) was subjected to the same hydrogen fluoride treatment and gel filtration column chromatography as in Example 1 to obtain 120 mg of the crude peptide. Then, 30 mg of this preparation was purified by HPLC to obtain 5.7 mg of Compound (XII) in a pure state.

Mass spectrum: 1863 ($M^+ + 1$)
Amino acid analysis:
Glx 2.2(2), Ser 1.1(1), Gly 1.2(1), Ala 2.2(2),
Tyr 2.0(2), Met 1.0(1), Cys 1.0(1), Ile 2.0(2),
Leu 1.2(1), Phe 1.1(1), Lys 2.0(2)

What is claimed is:

1. A peptide selected from the group consisting of peptides having the amino acid sequences represented by the following formulae (I) to (XII):

H—Val—Asp—Glu—Ala—Thr—Ile—Ile—Asp—Ile—Leu— (I)

Thr—Lys—Arg—Asn—Asn—OH

H—Thr—Lys—Arg—Asn—Asn—Ala—Gln—Arg—Gln— (II)

Gln—Ile—Lys—Ala—Ala—Tyr—OH

H—Ile—Lys—Ala—Ala—Tyr—Leu—Gln—Glu—Thr— (III)

Gly—Lys—Pro—Leu—Asp—Glu—Thr—Leu—Lys—Lys—Ala—

Leu—Thr—Gly—His—Leu—Glu—OH

H—Lys—Pro—Leu—Asp—Glu—Thr—Leu—Lys—Lys— (IV)

Ala—Leu—Thr—Gly—His—Leu—Glu—OH

H—Ile—Glu—Ile—Leu—Ala—Ser—Arg—Thr—Asn— (V)

Lys—Glu—Ile—Arg—Asp—Ile—OH

H—Thr—Thr—Arg—Ser—Tyr—Pro—Gln—Leu—Arg— (VI)

Arg—Val—Phe—Gln—Lys—Tyr—Thr—OH

H—Lys—Gly—Asp—Ile—Glu—Lys—Cys—Leu—Thr— (VII)
Ala—Ile—Val—Lys—Cys—Ala—OH

H—Lys—Cys—Leu—Thr—Ala—Ile—Val—Lys—Cys— (VIII)
Ala—Thr—Ser—Lys—Pro—Ala—OH

H—Ile—Val—Lys—Cys—Ala—Thr—Ser—Lys—Pro— (IX)
Ala—Phe—Phe—Ala—Glu—Lys—OH

H—Gly—Val—Gly—Thr—Arg—His—Lys—Ala—Leu— (X)
Ile—Arg—Ile—Met—Val—Ser—Arg—OH

H—Val—Ser—Arg—Ser—Glu—Ile—Asp—Met—Asn— (XI)
Asp—Ile—Lys—Ala—Phe—Tyr—OH and

H—Ile—Lys—Ala—Phe—Tyr—Gln—Lys—Met—Tyr— (XII)
Gly—Ile—Ser—Leu—Cys—Gln—Ala—OH

* * * * *

UNITED STATES PATENT AND TRADEMARK OFFICE
CERTIFICATE OF CORRECTION

PATENT NO. : 4,895,931

DATED : January 23, 1990

INVENTOR(S) : KEI OKAZAKI ET AL.

It is certified that error appears in the above-identified patent and that said Letters Patent is hereby corrected as shown below:

TITLE PAGE:

AT [56] REFERENCES CITED

U.S. Patent Documents, "4,778,304 11/1988 Marshall et al." should read --4,788,304 11/1988 Marshall et al.--.

COLUMN 1

Line 38, "respectively:" should read --respectively [hereinafter referred to as Compounds (I) to (XII)]:--.

COLUMN 6

Line 55, "Example" should read --Example 1--.

Signed and Sealed this

Fourth Day of June, 1991

Attest:

HARRY F. MANBECK, JR.

*Attesting Officer*      *Commissioner of Patents and Trademarks*